US00PP32755P2

(12) United States Plant Patent
Southwick

(10) Patent No.: US PP32,755 P2
(45) Date of Patent: Jan. 19, 2021

(54) CHERRY TREE NAMED 'SMS-1-CA-WA 2014-1'

(50) Latin Name: ***Prunus avium* L.**
Varietal Denomination: SMS-1-CA-WA 2014-1

(71) Applicant: S M S UNLIMITED, LLC, Lodi, CA (US)

(72) Inventor: Stephen M. Southwick, Lodi, CA (US)

(73) Assignee: SMS UNLIMITED, LLC, Lodi, CA (US)

( * ) Notice: Subject to any disclaimer, the term of this patent is extended or adjusted under 35 U.S.C. 154(b) by 0 days.

(21) Appl. No.: 16/602,481

(22) Filed: Oct. 16, 2019

(51) Int. Cl.
*A01H 5/08* (2018.01)
*A01H 6/74* (2018.01)

(52) U.S. Cl.
USPC ..... Plt./181
CPC ..... *A01H 6/7445* (2018.05)

(58) Field of Classification Search
USPC ..... Plt./181
CPC ..... A01H 5/085
See application file for complete search history.

*Primary Examiner* — Kent L Bell
(74) *Attorney, Agent, or Firm* — Randall Danskin, P.S.

(57) ABSTRACT

A new and distinct variety of sweet cherry tree, which is denominated varietally as 'SMS-1-CA-WA 2014-1' is described, with very high productivity and which produces early ripening fruit considered large in size and low in off-grade fruit types of deep suture, spur, and double fruit formations under the ecological conditions prevailing in Lodi, Calif.

12 Drawing Sheets

Latin name: *Prunus avium* L.

Variety denomination: The invention relates to a new, novel, and distinct variety of cherry tree, a *Prunus avium* L., with a variety denomination hereinafter as 'SMS-1-CA-WA 2014-1'.

SUMMARY

The new variety 'SMS-1-CA-WA 2014-1' (hereinafter abbreviated 'SMS-1') was discovered from an open pollination of seeds collected in 1998 from a proprietary sweet cherry selection 'SC-36a' (unpatented) located near Vina, Lodi, and Bakersfield, Calif. The seeds were stratified, testa removed, and then were germinated and planted in pots in 1999. After germination, the aforementioned seeds were grown in pots for 3 years until flowering. Fruit was first observed in 2002. A first asexual reproduction took place when buds were taken in that same year and propagated on *Prunus mahaleb* L. rootstock (unpatented) for further confidential trials conducted in Vina, Calif. starting in 2003. After two years of cropping in pots, buds were taken in a second asexual reproduction and grafted onto *Prunus mahaleb* L. seedling rootstock for further evaluation in Stockton, Calif. in 2004. Additional confidential trials similar to those described above were conducted starting in 2006 in Stockton, Calif., in 2011 in Bakersfield and Kingsburg, Calif. (USDA growing zones 9a, 9b), and in 2011 in Roosevelt, Wash. (USDA growing zones 7a, 7b). In 2007, the first fruit from trial growing fields were evaluated.

Throughout the aforementioned trials and various asexual propagations, the tree and fruit produced thereby were compared to the originally discovered plant. All characteristics of the original tree and its fruit were established and appears to have been transmitted to the aforementioned succeeding generations. The seed parent 'SC-36a' fruiting characteristics include larger fruit ripening 3 to 5 days before, with longer stems, and relatively free from deep suture and double fruit while consistently higher crop production compared with 'Brooks' sweet cherry. However, the 'SC-36a' fruit is prone to rain cracking and fruit surface discoloration prior and after packaging.

The present cherry tree variety 'SMS-1-CA-WA 2014-1' is an early fruiting variety ripening with 'Brooks' sweet cherry under the ecological conditions of the central valley of California. The new variety differs from a 'Brooks' cherry tree (U.S. Plant Pat. No. 6,676) and other sweet cherries within the same maturity period in the following manner. Productivity is very high, with concomitant large fruit size greater than 30 millimeters (mm), often larger than 32 mm, under normal cropping conditions and low percentage of off-grade fruit types (i.e., deep suture, fruit spurs, and doubles). Other features of the new variety include long stem and low acidity, allowing for earlier and easier harvest and generally higher levels of consumer acceptance. (Crisosto, Carlos H., Gayle M. Crisosto, Paul Metheney. "Consumer acceptance of 'Brooks' and 'Bing' cherries is mainly dependent on fruit SSC and visual skin color." Postharvest Biology and Technology 28:159-167.) The stems are tightly attached to the fruit of the new variety, while some other early selections (e.g., 'Coral', syn. 'Coral Champagne' unpatented) have short stems, small fruit size with a large crop, and poor stem retention, leading to many fruits being harvested and packaged without the stem, and not preferred in the market at this moment. In addition, 'SMS-1-CA-WA 2014-1' sweet cherry has fewer fruit with off-grade fruit types of deep suture, spur, and double fruit formations when compared with 'Brooks' (Table 1) and 'Coral Champagne' growing under identical conditions in the Southern San Joaquin Valley areas of California. Comparisons to 'Coral Champagne' described herein are based on personal observation made by the breeder though not quantified in Table 1.

TABLE 1

Comparison of 'SMS-1-CA-WA 2014-1' and 'Brooks' sweet cherry soluble solids (%), relative size (mm), crop load rating, and off-grade (% fruit with deep suture, fruit spurs, and fruit doubles) at early harvest maturity in 2018 and 2019 in Lodi, Calif.

| Variety Sweet Cherry | Soluble solids (%) | Fruit size (mm) | Crop Load Rating** | Off-grade (% of fruit with deep suture, spurs, and doubles) |
|---|---|---|---|---|
| 2019 'SMS-1-CA-WA 2014-1' | 21.1 | 30.3 | 9.3 | 0.47 |
| 2019 'Brooks' | 17.4 | 26.7 | 7.8 | 8.90 |
| 2018 'SMS-1-CA-WA 2014-1' | 20.4 | 31.6 | 7.6 | 0.35 |
| 2018 'Brooks' | 17.9 | 27.2 | 2.4 | 2.70 |

**Crop load rating was defined as follows on 5 year-old second generation trees growing in Lodi, Calif. May 2019 as: 0-10, where 0 = 0 pounds of fruit and 10 = 60 pounds of fruit. All numbers are averages of 100 fruit from each of 5 replicate trees with fruit color based on Centre Technique Interprofessionnel des Fruits et Légumes (CTIFL) code colour of 4 and 5.

BRIEF DESCRIPTION OF THE DRAWINGS

The accompanying drawings are color photographs of the new cherry tree variety on the dates indicated and under the ecological conditions prevailing at the locations indicated. The mother tree began growing in 1999, the first generation begin growing in 2002, and the second generation began growing in 2004.

Figure 1:
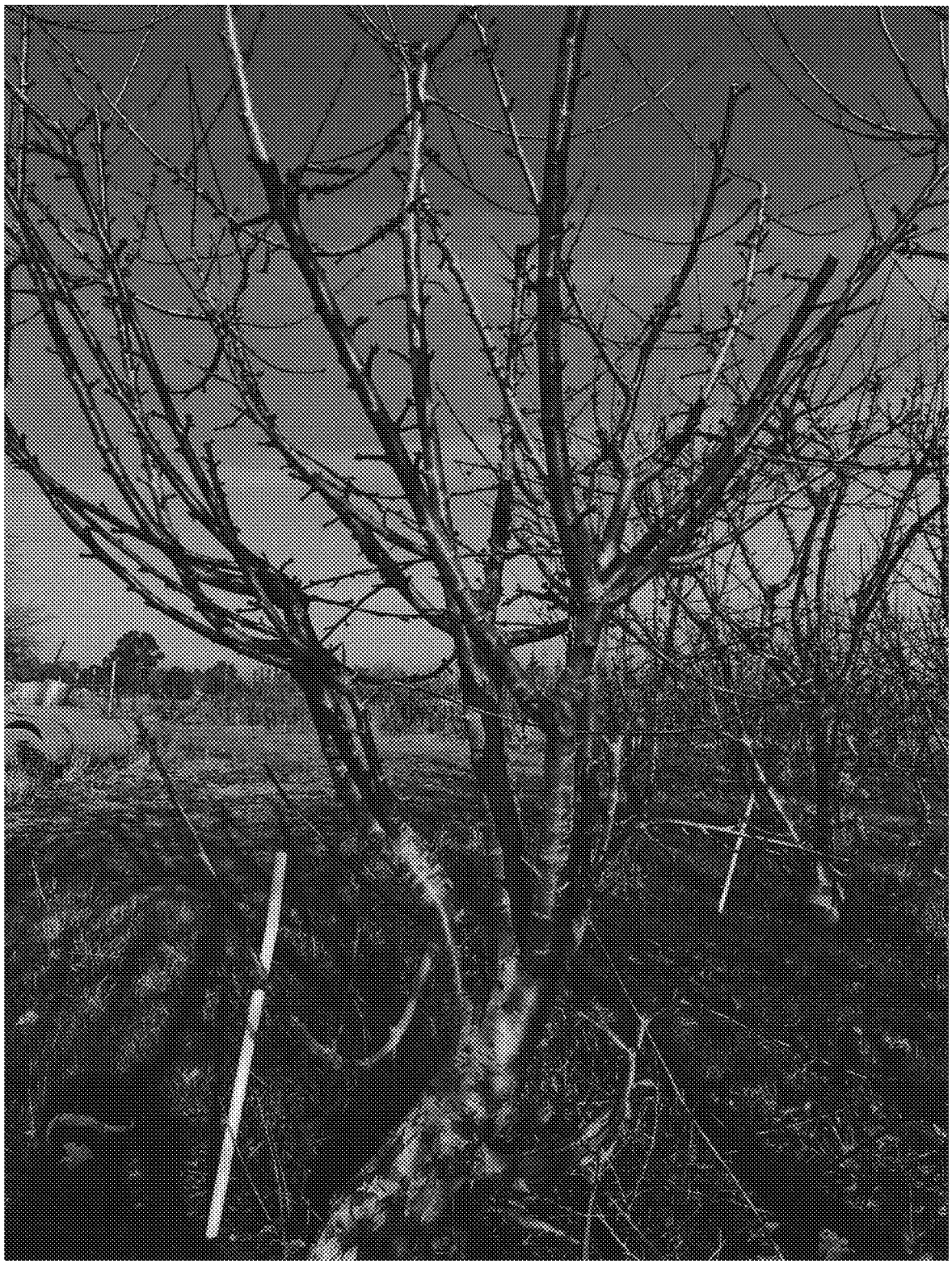
FIG. 1 is a color photograph showing the 'SMS-1-CA-WA 2014-1' mother tree in Stockton, Calif., January 2015.
Figure 2:
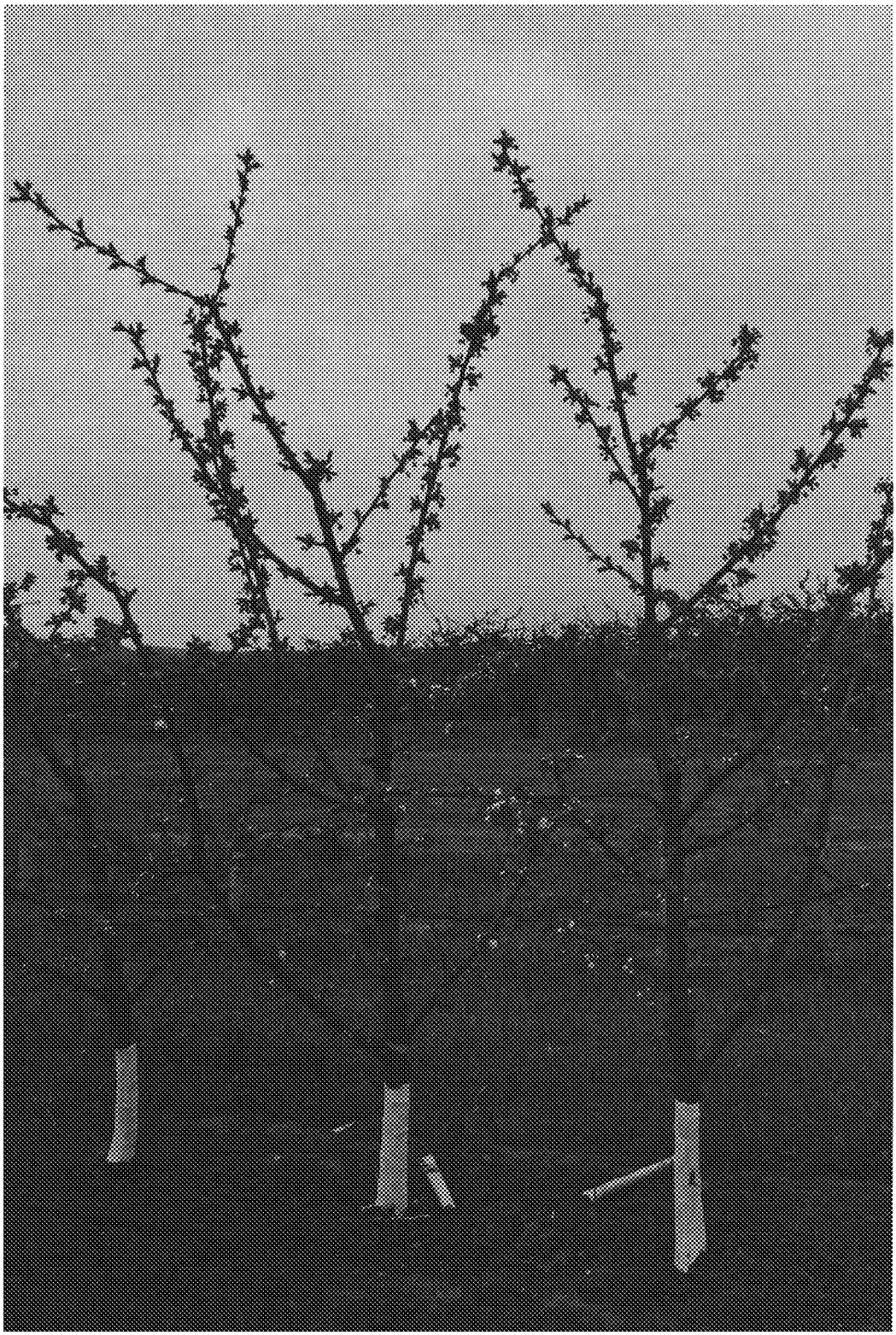
FIG. 2 is a color photograph showing early bloom bud break of 'SMS-1-CA-WA 2014-1' second generation trees in Roosevelt, Wash., April 2018.
Figure 3:
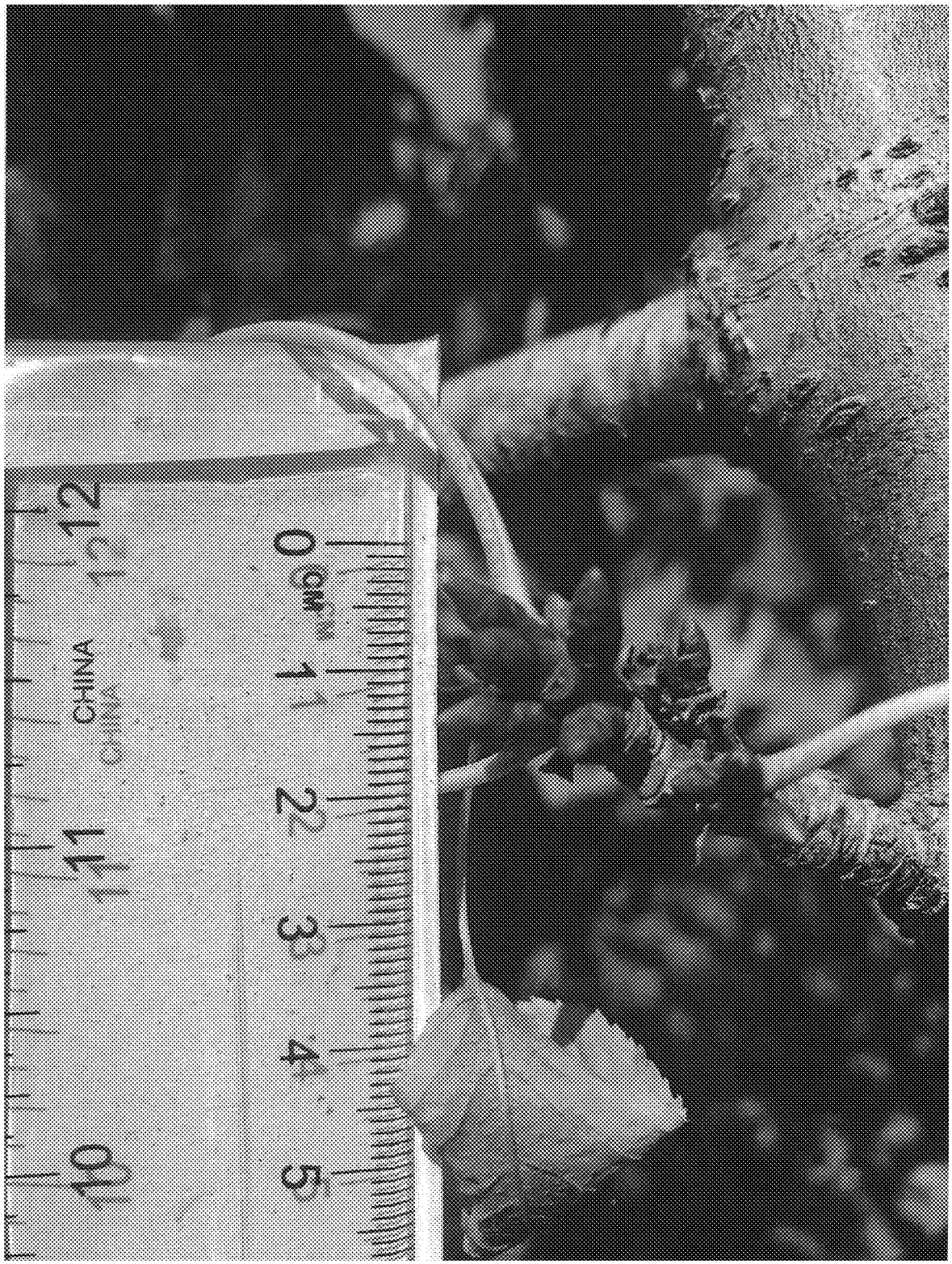
FIG. 3 is a color photograph showing resting/dormant buds of 'SMS-1-CA-WA 2014-1' in Stockton, Calif., January 2015.
Figure 4:
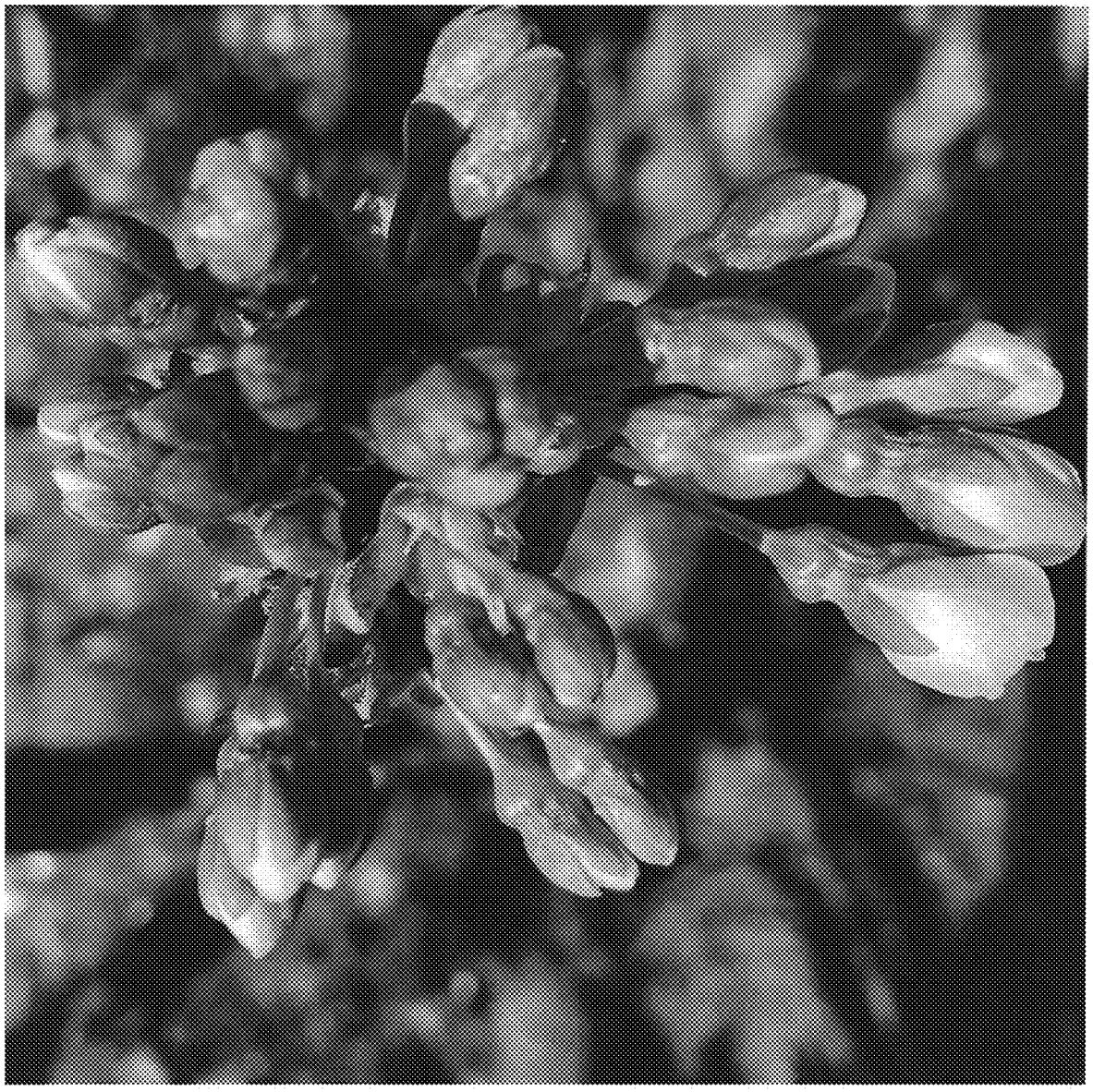
FIG. 4 is a color photograph showing early bloom bud break of the 'SMS-1-CA-WA 2014-1' mother tree in Stockton, Calif., Mar. 19, 2019.
Figure 5:
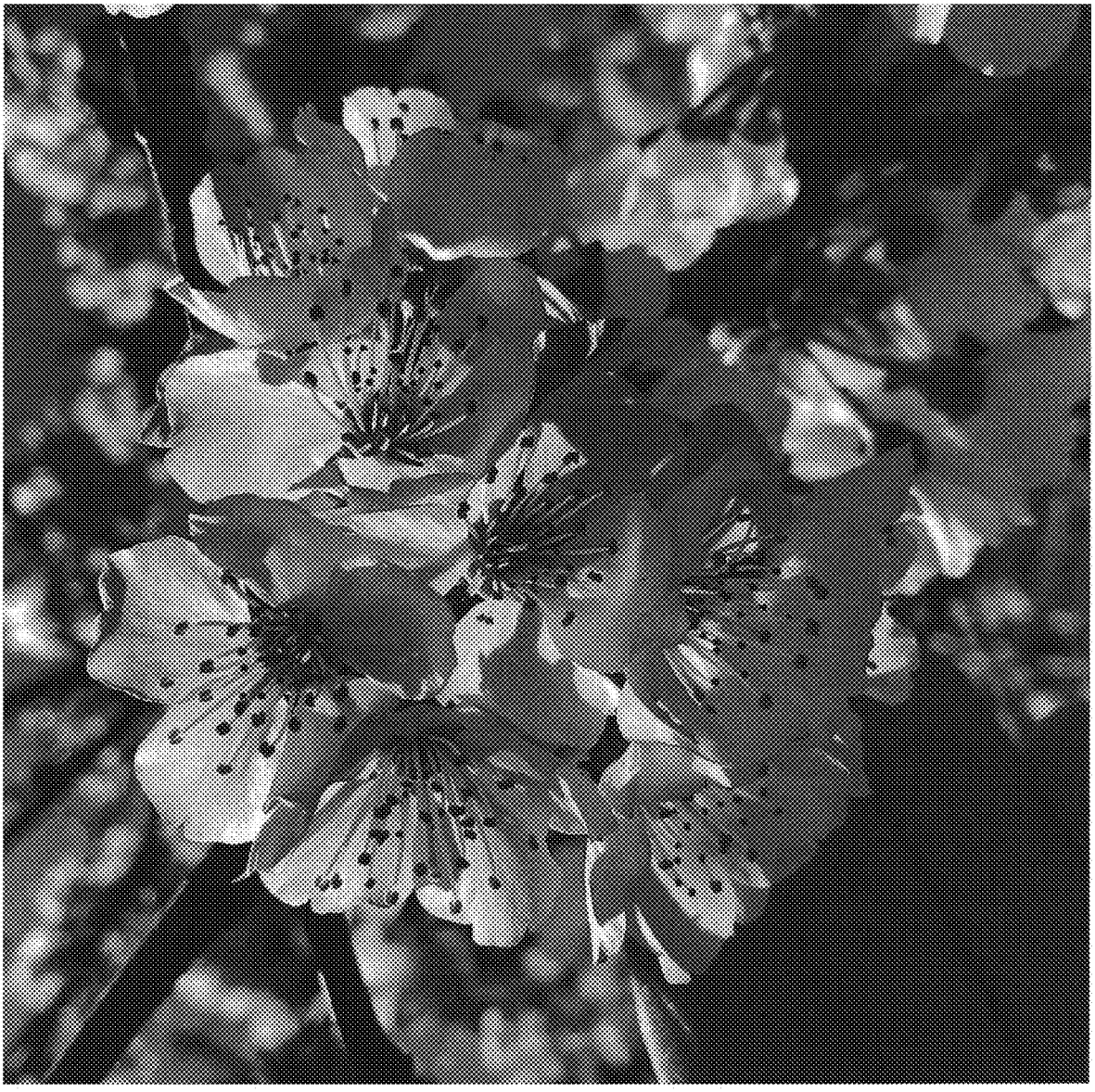
FIG. 5 is a color photograph showing full bloom of blossom cluster of the 'SMS-1-CA-WA 2014-1' mother tree in Stockton, Calif., Mar. 29, 2019.
Figure 6:
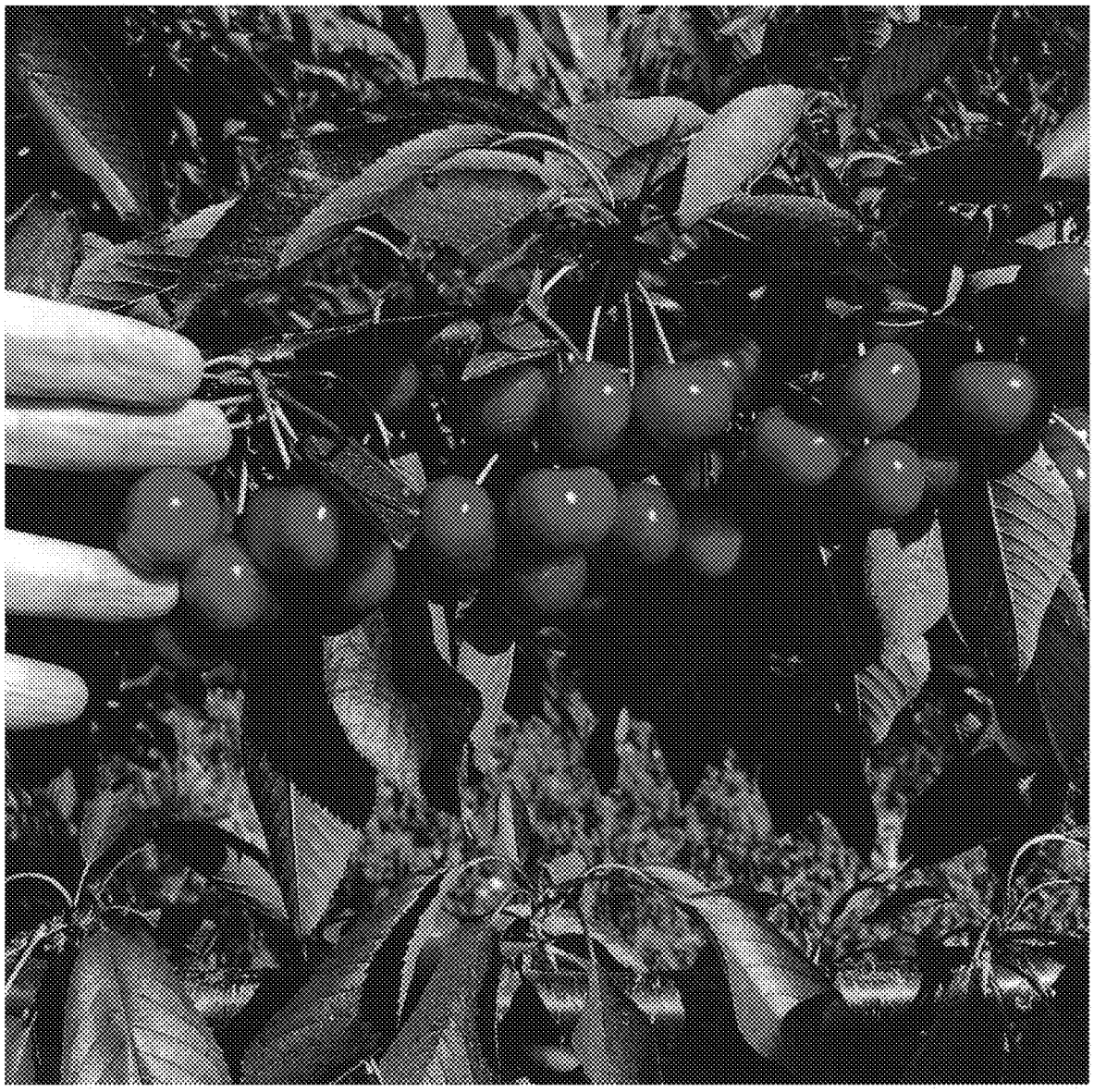
FIG. 6 is a color photograph showing fruit of the 'SMS-1-CA-WA 2014-1' mother tree in Stockton, Calif., May 10, 2019.
Figure 7:
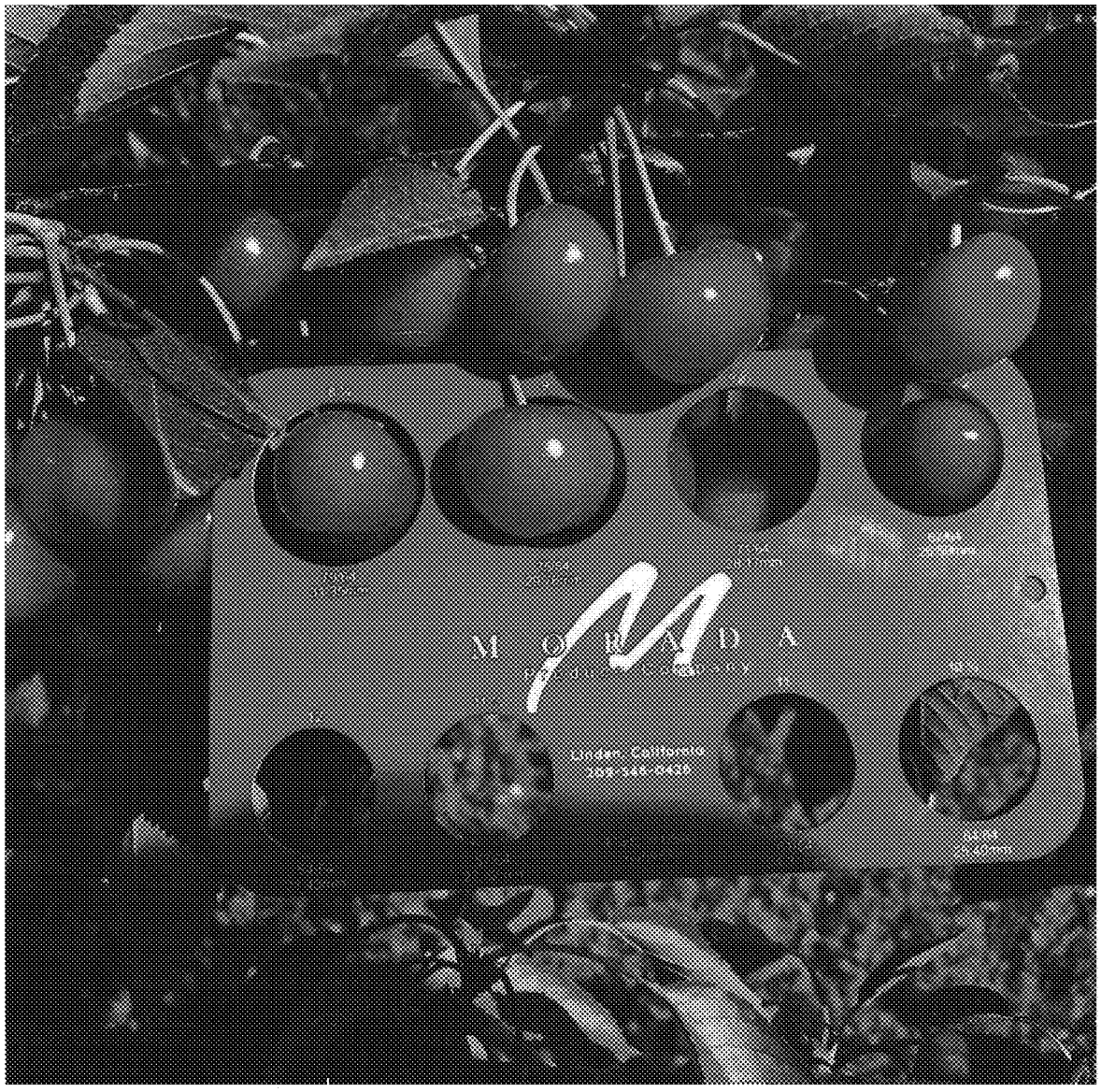
FIG. 7 is a color photograph showing large fruit size, consistently found even with heavy cropping, of the 'SMS-1-CA-WA 2014-1' mother tree in Stockton, Calif., May 10, 2019.
Figure 8:
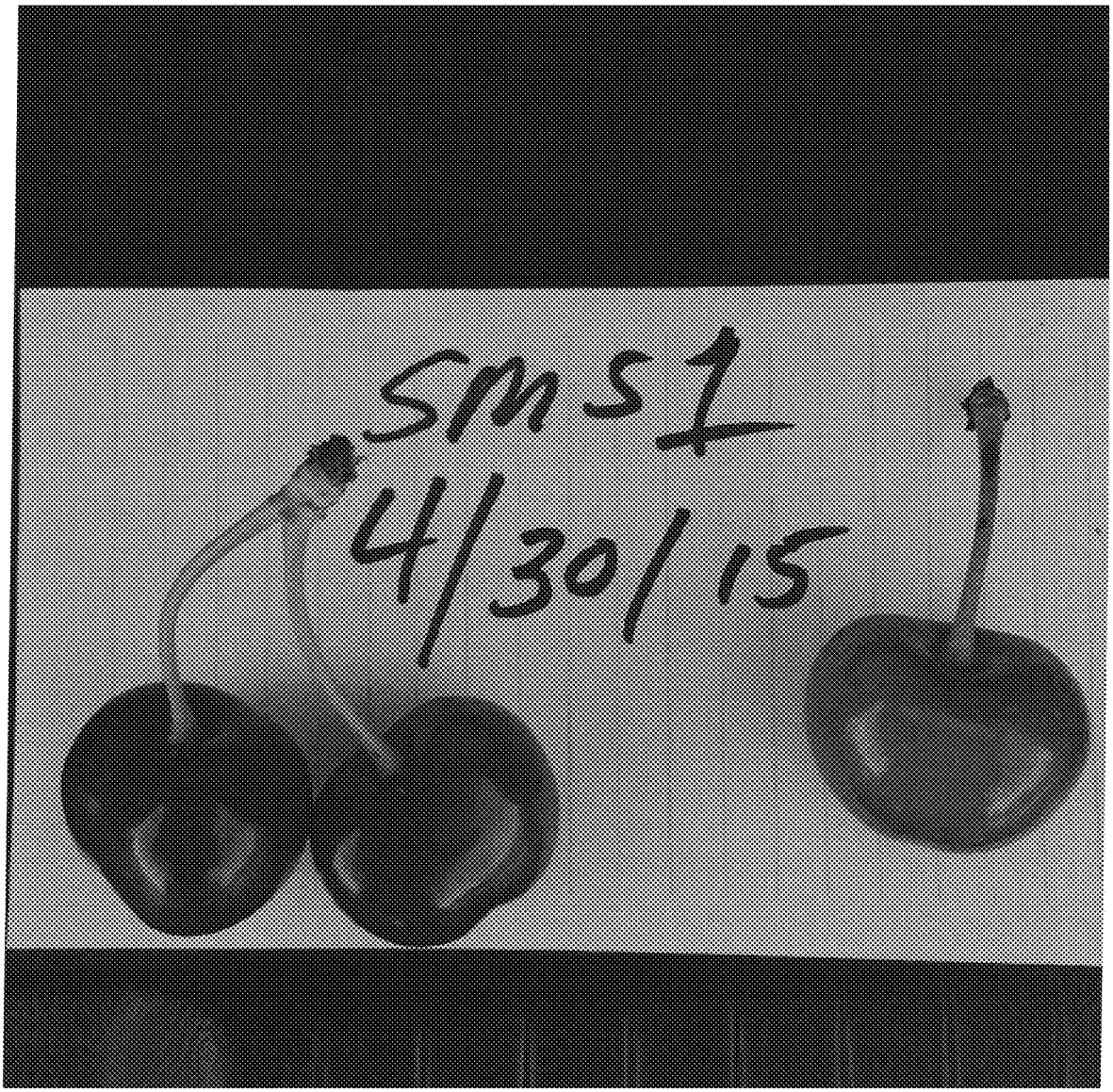
FIG. 8 is a color photograph showing fruit of the 'SMS-1-CA-WA 2014-1' mother tree as harvestable cherry fruit at harvest maturity with no rest breaking agents applied.
Figure 9:
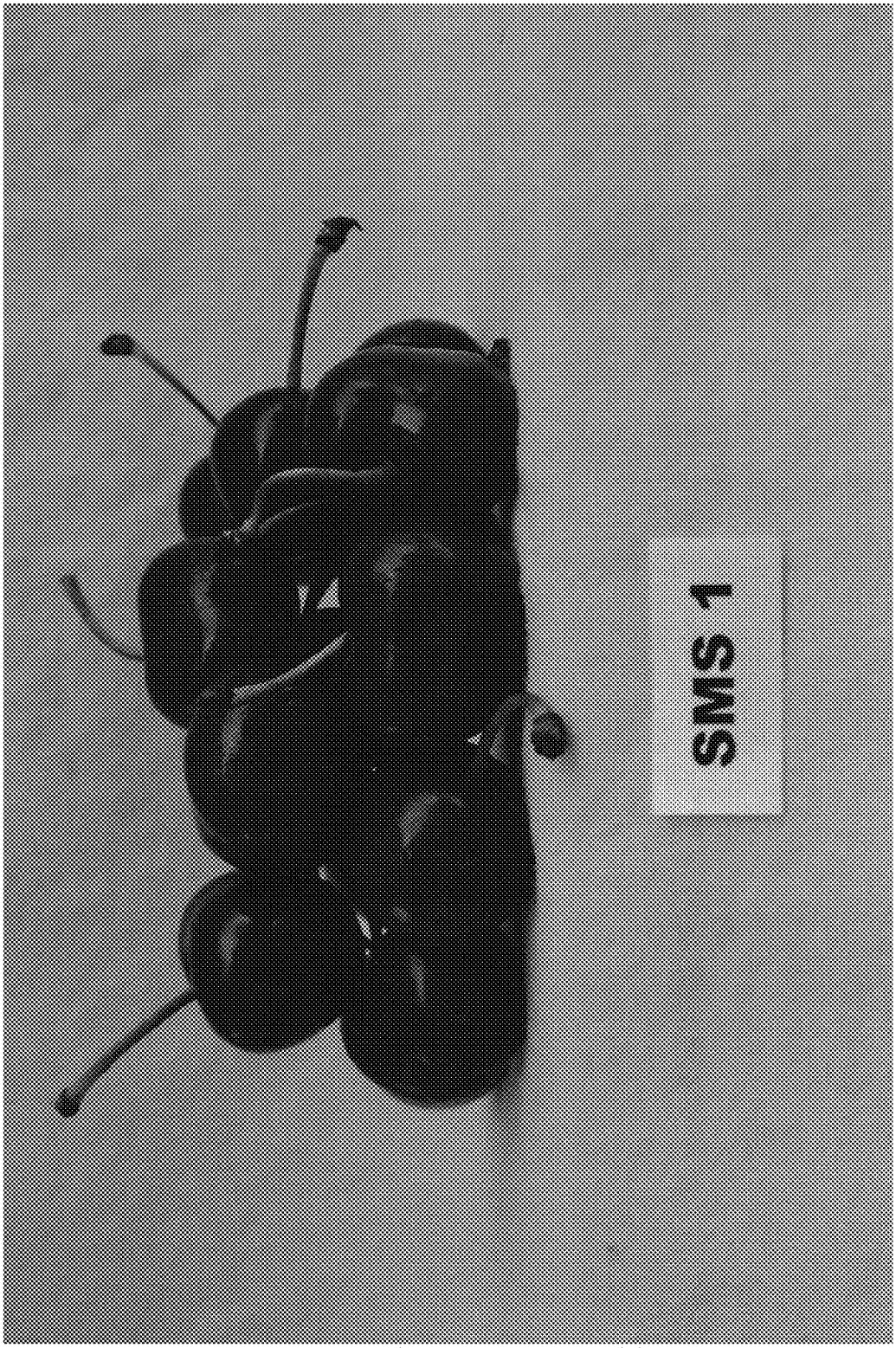
FIG. 9 is a color photograph showing fully mature 'SMS-1-CA-WA 2014-1' first generation fruit.
Figure 10:
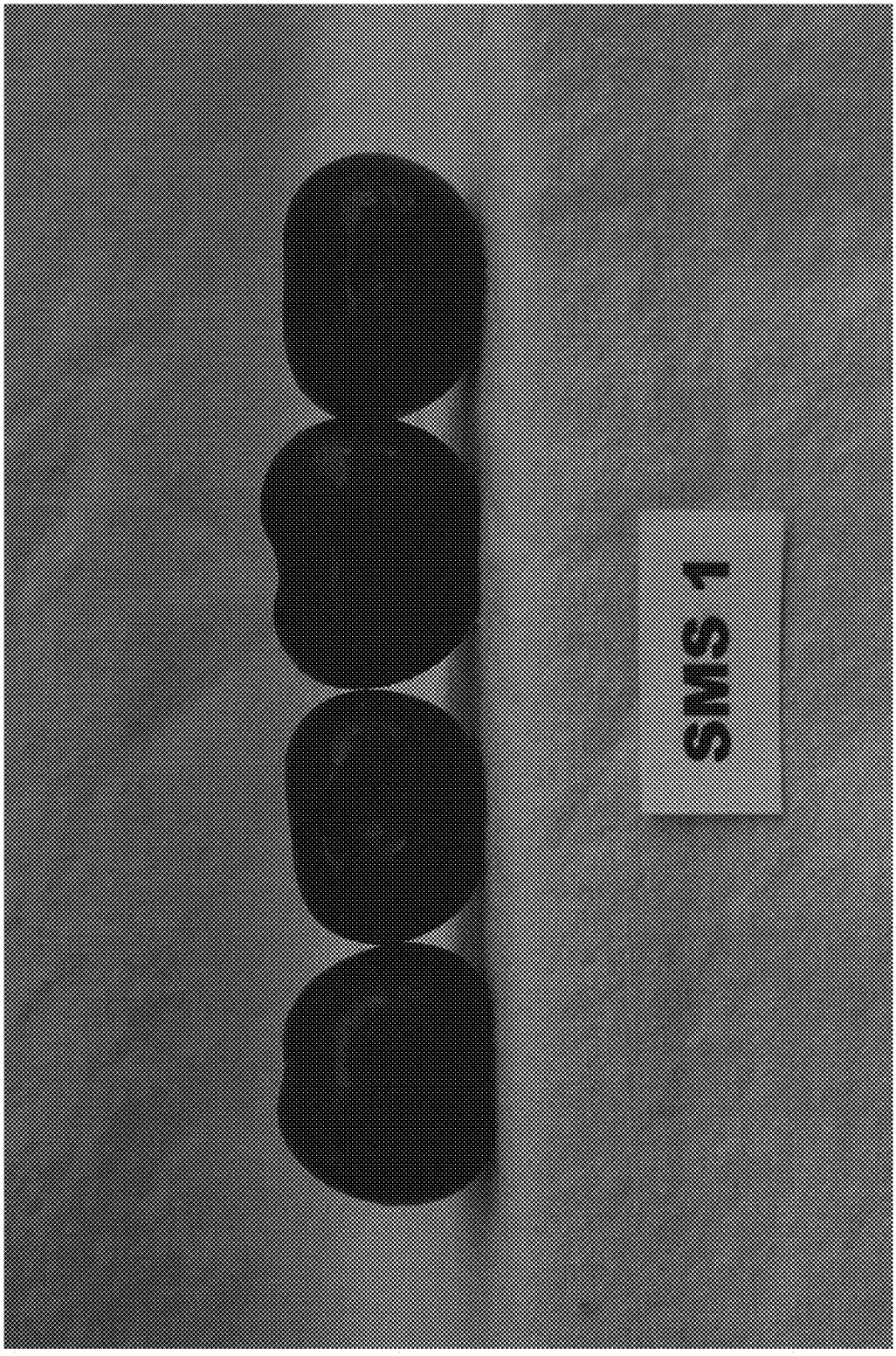
FIG. 10 is a color photograph showing top, side, and bottom views of first generation 'SMS-1-CA-WA 2014-1' cherries at harvest maturity.
Figure 11:
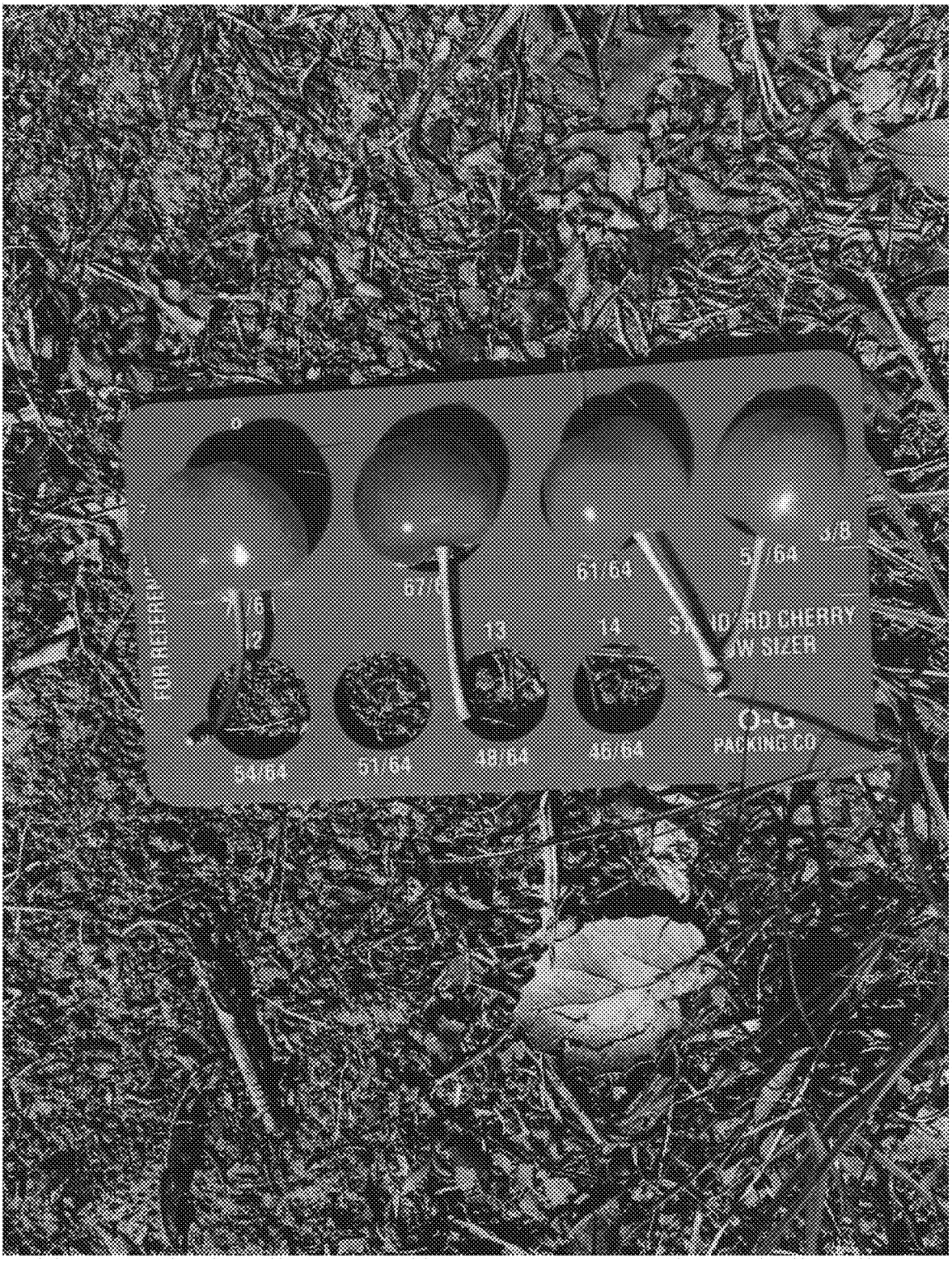
FIG. 11 is a color photograph showing two first generation 'SMS-1-CA-WA 2014-1' cherries on the left (row size 9 and 10) and two 'Brooks' cherries on the right (row size 11 and 11.5). Indicative of relative size and maturity, the 'SMS-1-CA-WA 2014-1' cherries are larger and slightly more mature compared with 'Brooks.'
Figure 12:
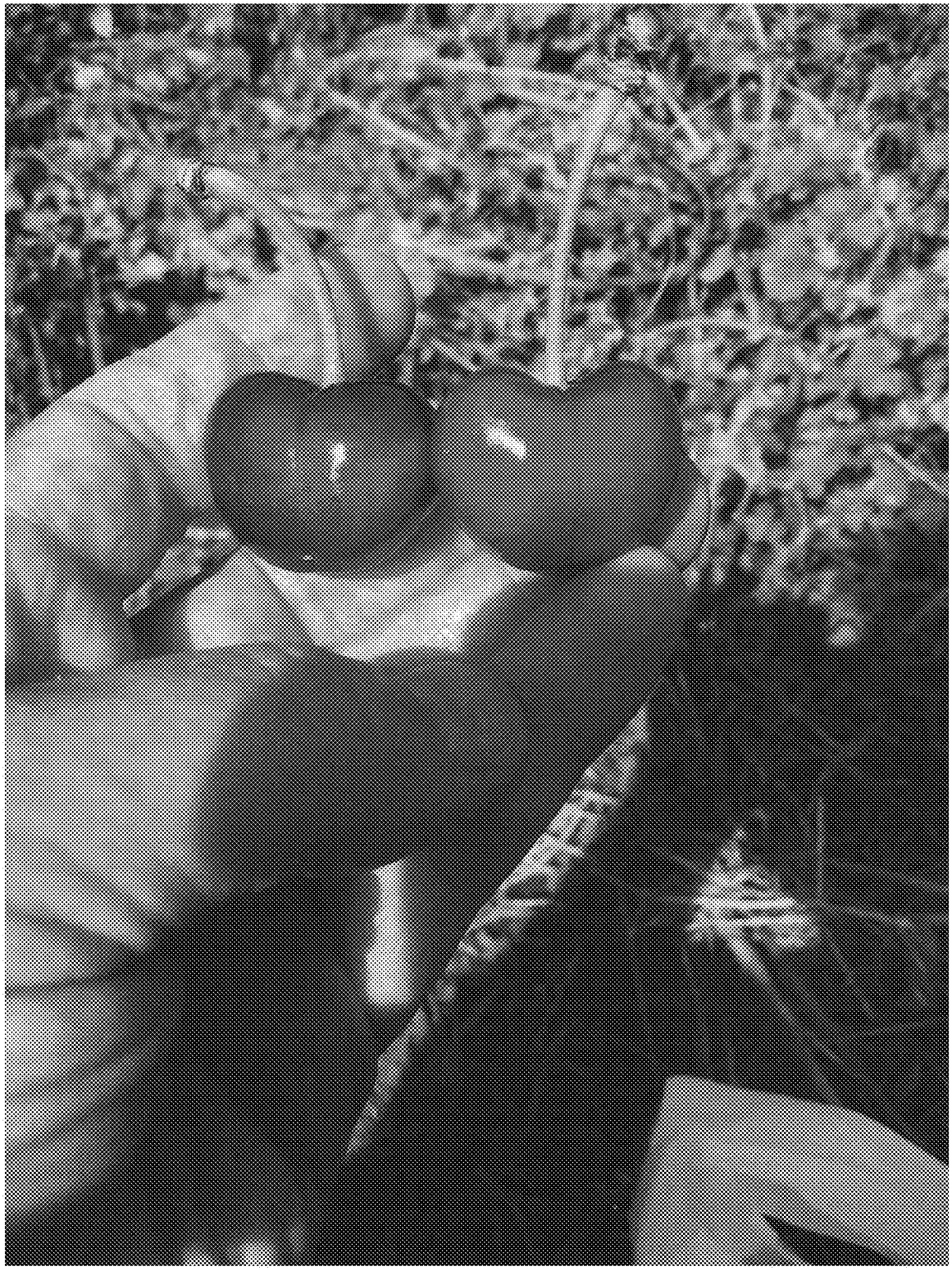
FIG. 12 is a color photograph showing first generation 'SMS-1-CA-WA 2014-1' cherry relative size (30 mm) and shape at early harvest maturity.

The colors in these photographs are as nearly true as is reasonably possible in a color representation of this type. Due to variations in color printers and/or chemical development, processing and printing, the colors of the plant parts depicted in these photographs may, or may not, be accurate when compared to the actual specimen. For this reason, color references are made to the color plates (Royal Horticultural Society Colour Chart, Fourth Edition, 2001, hereinafter, "R.H.S.") and descriptions provided.

DETAILED BOTANICAL DESCRIPTION

Not a Commercial Warranty. The following detailed description was prepared solely to comply with the provisions of 35 U.S.C. § 112, and does not constitute a commercial warranty (either expressed or implied) that the present variety will, in the future, display the botanical, horticultural, or other characteristics set forth herein. Therefore, this disclosure may not be relied upon to support any future legal claims including, but not limited to, breach of warranty of merchantability, or fitness for any particular purpose, or non-infringement, which is directed in whole, or in part, to the present new variety of plant.

Referring more specifically to the botanical features of this new and distinct variety of cherry tree, the following has been observed during the eleventh year of growth under the ecological conditions prevailing at the breeder's property, which is located near Lodi, Calif. A second generation, four-year-old tree growing on *Prunus mahaleb* L. rootstock in Roosevelt, Wash. was used to validate fruit size and other flowering and fruiting characteristics in another important sweet cherry growing region in the Columbia River Basin along the Washington-Oregon state border.

Tree: General.

*Size*.—Considered moderate for age and rootstock, 411.5 centimeters (cm) (13.5 feet) tall and 70 cm in diameter.

*Vigor*.—Considered moderately high.

*Branching habit*.—Upright and spreading.

*Density*.—Considered moderate.

*Form*.—Trained to open vase.

*Hardiness*.—Considered hardy for Lodi, Calif.

*Production*.—Considered moderately high to high in precocity with a yield of 16,335 pounds of fruit per acre in the fifth growing season based on 272 trees per acre.

*Bearing*.—Considered annual.

Tree: Trunk (measured at harvest maturity).

*Size*.—Circumference at 30 cm above ground is 70 cm.

*Texture*.—Mostly smooth, beginning to develop rough texture for age.

*Color*.—From the RHS Greyed-Orange Group 166A.

*Lenticels*.—Numerous and prominent with a horizontal orientation. Length ranges from 15.4 mm to 52.7 mm with an average of 27.8 mm. Width ranges from 1.7 mm to 8.6 mm with an average of 4.1 mm. Number of lenticels averages 9 per 9 square centimeters. Color is from the RHS Greyed-Yellow Group 166C.

Tree: Branches (measured at harvest maturity).

*Scaffold branches*.—Texture — Mostly smooth. Size — Circumference at 10 cm from trunk union ranges from 26 cm to 30 cm with an average of 29 cm. Angles as trained range from 25 to 70 degrees from horizontal. Color — From the RHS Greyed-Orange Group 174A. Lenticels — Numerous, averaging 14 per 9 $cm^2$. Length ranges from 16.4 mm to 33.6 mm with an average of 24.3 mm. Width ranges from 3.6 mm to 8.8 mm with an average of 6.7 mm. Center color is from the RHS Greyed-Purple Group N186C; outer margin color from the RHS White Group N155A.

*Second year fruiting branches*.—Texture — Smooth. Diameter — Ranges from 5.0 mm to 6.8 mm at mid-point of growth with an average of 6.4 mm. Color — From the RHS Greyed-Orange Group 174A. Lenticels — Moderate in number averaging 13 per running cm; are oval in shape and range from 1.5 mm to 2.1 mm in length and 1.0 mm to 1.3 mm in width. Color from the RHS Greyed-Orange Group 165D.

*Current year branches*.—Texture — Smooth. Size — Length ranges from 37.5 cm to 62.5 cm with an average of 47.8 cm. Diameter ranges from 4.6 mm to 5.6 mm with an average of 5.1 mm at half-way point. Color — From the RHS Greyed-Orange Group N167A. Internode length — Ranges from 3.6 cm to 5.2 cm with an average of 4.4 cm. Lenticels — Moderate in number averaging 10 per running cm; small, round and ranging 0.2 mm-0.6 mm in diameter; color is from the RHS Greyed-Orange Group N167D.

Foliage: Leaves (measured from midpoint of actively growing current season's growth at harvest maturity).

*Blade*.—Size — Length ranges from 13.5 cm to 16.2 cm and averaging 15.2 cm; width ranges from 5.0 cm to 5.8 cm with an average of 5.4 cm. Thickness averages 0.23 mm. Texture — Upper surface is smooth and leathery, lower surface is smooth with vein protruding above surface. Tip — Acuminate. Base — Rounded. Form/shape — Oblong with acuminate tip. Margin — Bi-serrate. Blade color — Upper surface from the RHS Yellow-Green Group 146A; lower surface color from the RHS Yellow-Green Group 146B.

*Midvein*.—Considered medium large and prominent averaging 1.4 mm in diameter at mid-point of blade with a range of 1.3 to 1.5 mm. Apex half from the RHS Greyed-Green Group 195D, basal half from the RHS Greyed-Purple Group 184A.

*Petiole*.—Averages 3.4 cm in length with a range of 3.0 to 3.6 cm; diameter at mid-point ranges from 1.8 mm to 2.2 mm with an average of 2.1 mm; upper surface color is from the RHS Greyed-Purple Group 183A; lower surface color is from the RHS Greyed-Purple Group 183D. A 0.3 mm depth, 1.0 mm wide groove runs the full length of upper surface.

*Glands*.—Present, kidney-shaped, and averaging 2.7 mm in length by 1.5 mm in width; 0-3 per petiole, mostly 2 alternating in position along groove of petiole and located from 0 mm to 6.2 mm from blade base; color is from the RHS Greyed Group 178A.

*Stipules*.—Not present.

*Attitude*.—Somewhat drooping. Blades folded upward.

*Leaf arrangement on stem*.—Alternate.

Flower buds (as measured at full bud swell):

*Spur length*.—Ranges from 17.6 mm to 39.2 mm with an average of 27.1 mm.

*Bud shape*.—Cordate.

*Number buds per fruiting spur*.—Ranges from 5 to 7 mostly 6; bud length ranges from 7.6 mm to 10.0 mm with an average of 8.8 mm; bud diameter ranges from 4.0 mm to 5.8 mm with an average of 4.8 mm. Scale color from the RHS Greyed-Orange Group 174A.

Flowers:

*Attitude*.—Bloom stands out with moderate droop.

*First bloom*.—March 17 under the ecological conditions prevailing in Lodi, Calif. Three-year average is March 16.

*Full bloom*.—March 26 under the ecological conditions prevailing in Lodi, Calif. Three-year average is March 27.

*Size*.—Bloom diameter when fully open averages 3.7 cm and is considered open.

*Bloom count*.—Three blossoms per bud.

*Petals*.—Five in number; color is from the RHS White Group 155C; average length is 14.9 mm; average width is 16.0 mm. Petal shape is round, margins are smooth, both upper and lower texture is 'lightly ruffled,' base is rounded and the apex is emarginate. When fully open, petals are generally touching.

*Nectary color*.—Color is from the RHS Yellow-Green Group 153D.

*Stamens*.—Filament — Average number per bloom is 32; color is from the RHS White Group 155C. Average length is 8.1 mm. Anther — Kidney shaped with average size is 1.2 mm long and 1.0 mm wide.

*Pollen*.—Abundant; color is from the RHS Greyed-Orange 163B.

*Carpel*.—Style — Average length is 11.8 mm; color is from the RHS Yellow-Green Group 149D. Stigma — Clubbed and considered round in shape. Diameter ranges from 0.7 to 0.9 mm and is from the RHS Yellow-Green Group 149C.

*Sepals*.—Five in number; deltoid in shape, laid back over thalmus, margins are smooth, both upper and lower texture is smooth, and apex is rounded; average base width is 5.4 mm; average length is 6.8 mm; color is from the RHS Yellow-Green Group 144C with outside and inside tip highlights from the RHS Greyed-Red Group 180A.

*Peduncle*.—Average length is 2.6 cm, average diameter at mid-length is 1.0 mm; color is from the RHS Green Group 145B.

*Thalmus*.—Urn shaped; average depth is 7.2 mm, average width at the opening is 4.5 mm. Color from the RHS Yellow-Green Group N144B.

Fruit:

*Maturity*.—Harvest maturity May 8 under the ecological conditions prevailing in Lodi, Calif. The three-year average is May 6.

*Quantity per cluster*.—One to five fruit per bud or cluster.

*Size*.—Considered large; average apical diameter is 24.8 mm; average axial side to side diameter is 31.7 mm, average suture axil diameter is 24.6 mm.

*Weight*.—10.8 to 16.9 grams (g), average 12.6 g.

*Form*.—Considered oblate. Sides uniform.

*Suture*.—Lightly distinct, on the "back" side. Suture is a slight depression that is 0.1 mm in depth, and 0.3 mm to 0.4 mm wide.

*Base*.—Uniform cordate in shape, width averages 12.8 mm, depth averages 4.3 mm.

*Apex*.—Rounded ending in slight distinct depression of 1.0 to 2.0 mm marked by a russetted dot 1.0 mm to 1.2 mm in diameter.

*Peduncle*.—Length ranges from 31.7 mm to 45.9 mm with an average length of 40.2 mm; diameter at mid-point averages 1.1 mm; color is from the RHS Yellow-Green Group 144A.

*Skin*.—Thickness — Considered thin, 0.04 to 0.06 mm. Texture — Surface is smooth and clear, melting in mouth. Tenacity — Very tenacious to flesh. Tendency to crack — Less than 'Brooks', but not unlike other commercially grown cherries in California. Varies with duration of rainfall, crop load and maturity of fruit with rain event. Down — Wanting. Color — Uniform and from the Greyed-Purple Group 186C.

*Flesh*.—Color — From the Greyed-Purple Group 186C. Surface of pit cavity color — From the Greyed-Purple Group 186C. Texture — Firm, melting. Fibers — Considered lightly fibrous. Pit tenacity — Very little, easily separated from flesh with light retention around suture. Ripens — Evenly. Flavor — Sweet and sub acid. Aroma — Mild cherry like. Eating quality — Excellent.

*Stone*.—Type — Light cling type. Size — Considered medium; averages 10.7 mm base to apex, 8.1 mm wide shoulder to shoulder, and 7.5 to 10.1 mm wide suture to suture. Form — Broad elliptic. Base — Rounded. Apex — Rounded. Sides — Equal (uniform). Surface — Smooth. Ventral Edge — suture is slightly raised 0.5 mm and is subtended by two low ridges converging basally and apically that averages 4.9 mm and 1.5 mm in height at the mid-point. Dorsal Edge — suture is raised 1.0 mm. Color — From the RHS Greyed-Yellow Group 161A. Tendency to split — None observed.

*Kernel*.—Shape — Considered obtuse. Base — Rounded. Apex — Acute. Size — Length ranges from 6.6 to 7.3 mm with an average of 7.0 mm. Width ranges from 4.1 to 4.5 mm with an average of 4.3 mm. Thickness ranges from 2.1 to 3.1 mm with an average of 2.9 mm. Color — From the RHS Greyed-Orange Group 164B. Taste — Bitter, almond-like. Viability — 100% kernel development observed, viable kernel germination unknown.

*Pollination requirements*.—Pollination alleles $S_3$ $S_9$.

*Market use of fruit*.—Early season, premium fresh market.

*Storability of fruit*.—Limited testing, but, at the moment, shows no unusual characteristics compared with other commercial early season sweet cherry varieties growing in California.

*Resistance to pests and disease*.—Shows no unusual susceptibility nor resistance to any diseases and/or plant or fruit pests of sweet cherry found in the San Joaquin Valley of California or in South Central Washington State.

*Shipping quality*.—Limited testing, but, at the moment, shows no unusual characteristics compared with other commercial early season sweet cherry varieties growing in California.

Although the new variety of cherry tree possesses the described characteristics when grown under the ecological conditions prevailing in Stockton and Lodi, Calif. and South Central Washington, Klickitat County, it should be understood that variations are to be expected in the usual magnitude and characteristics incident to changes in growing conditions, fertilization, pruning, pest control, frost, climatic variables, and horticultural management.

Having thus described and illustrated a new variety of sweet cherry tree, what is claimed to secure a plant Letters Patent is:

1. A new and distinct variety of sweet cherry tree, substantially as illustrated and described, which is characterized principally as to novelty by very high productivity and by producing early ripening fruit considered large in size and low in off-grade fruit types of deep suture, spur, and double fruit formations under the ecological conditions prevailing in Lodi, Calif.

* * * * *